United States Patent
Zakri et al.

(10) Patent No.: US 10,017,560 B1
(45) Date of Patent: Jul. 10, 2018

(54) NANOBODY AGAINST BEGOMOVIRUSES

(71) Applicant: KING SAUD UNIVERSITY, Riyadh (SA)

(72) Inventors: M. Adel Zakri, Riyadh (SA); Abdullah Abdulaziz Al-Doss, Riyadh (SA); Mohammed Ali Al-Saleh, Riyadh (SA); Ahmed Abd Elrahim Ali, Riyadh (SA); Basem Sayed Abbas Ahmed, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/815,569

(22) Filed: Nov. 16, 2017

(51) Int. Cl.
*C07K 16/08* (2006.01)
*C12N 15/82* (2006.01)
*A01N 37/46* (2006.01)

(52) U.S. Cl.
CPC ............ *C07K 16/081* (2013.01); *A01N 37/46* (2013.01); *C12N 15/8283* (2013.01); *C07K 2317/569* (2013.01)

(58) Field of Classification Search
None
See application file for complete search history.

(56) References Cited

U.S. PATENT DOCUMENTS

| | | | |
|---|---|---|---|
| 9,005,963 | B2 | 4/2015 | Blanchetot et al. |
| 2016/0075769 | A1 | 3/2016 | Verheesen et al. |

FOREIGN PATENT DOCUMENTS

| | | |
|---|---|---|
| CN | 102702349 A | 10/2012 |
| WO | 9749805 A2 | 12/1997 |
| WO | 02085945 A2 | 10/2002 |
| WO | 2016071438 A2 | 5/2016 |

OTHER PUBLICATIONS

Safarnejad, M. R. et al., Antibody-Mediated Resistance Against Plant Pathogens, Biotechnology Adv. 29:6 pp. 961-971 (2011).
Al-Saleh, M., et al., Molecular Characterization of a Naturally Occurring Intraspecific Recombinant Begomovirus with Close Relatives Widespread in Southern Arabia, Virology J. 11:103 (2014).
Ghannam, A., et al., Camelid nanobodies with high affinity for broad bean mottle virus: a possible promising tool to immunomodulate plant resistance against viruses, Plant Mol. Bio. 87:4-5 pp. 355-369 (2015).

*Primary Examiner* — Elizabeth F McElwain
(74) *Attorney, Agent, or Firm* — Richard C. Litman

(57) ABSTRACT

A nanobody directed against begomoviruses is capable of selectively binding to ToLCSDV viral particles, TYLCV particles, and/or other begomoviruses. The nanobody includes an amino acid sequence of SEQ ID NO: 2.

12 Claims, 3 Drawing Sheets

FIG. 3

NANOBODY AGAINST BEGOMOVIRUSES

The Applicants hereby incorporate by reference the sequence listing contained in the ASCII text file titled 32903_25_SequenceListing_ST25.txt, created Oct. 30, 2017 and having 2 KB of data (_ KB on disk).

BACKGROUND

1. Field

The disclosure of the present patent application relates to detection and disruption of begomovirus, and particularly to a nanobody against Tomato Leaf Curl Sudan Virus and other begomoviruses. More specifically, the subject matter relates to detection of Tomato Leaf Curl Sudan Virus (ToLCSDV) and Tomato Yellow Leaf Curl Virus (TYLCV) using a specific Variable domain (VHH) of the heavy chain antibody (Nb-To2) selected from an Arabian camel VHH library. This nanobody may be used to specifically detect ToLCSDV and TYLCV, or it may be cloned into transgenic plants to provide resistance to ToLCSDV, TYLCV, and other begomoviruses' infections.

2. Description of the Related Art

Plant viruses pose a significant threat to agricultural crops. Yield loss due to plant viruses can be huge and this translates into huge economic losses every day, for both small and large farmers. Typical strategies to combat plant viruses include chemical control, development of resistant cultivars by conventional breeding, preventative practice and, a growing array of genetic engineering and biotechnology strategies. Genetically modified plants are a safe and environmentally clean technology that can lessen the dependence on other industries, e.g. companies supplying pesticides.

The ectopic expression of antibodies in plants by genetic modification is a particularly powerful strategy, as antibodies can be designed to target any pathogen. Full-sized antibodies and various fragments and combinations of functional segments can be produced in plants to detect, disrupt or modulate viral disease vectors. Antibody fragments or strategically designed recombinant antibodies provide advantages of smaller size, allowing for increased tissue penetration and mobility, and more reliable folding and assembly, as well as more flexibility in potential applications.

In addition to conventional $H_2L_2$-type IgGs, camelid sera includes antibodies that have two heavy chains and no light chains, also called H chain-only antibodies (HCAbs). Each heavy chain includes a single monomeric variable domain (VHH) that is approximately 2.5 nm in diameter and 4.2 nm in length. These nanometer-sized antibody fragments, also known as nanobodies, are much smaller than full-sized immunoglobulins and other recombinant forms of antibodies such as scFv and Fab and additionally display improved resistance to denaturing stresses such as heat, detergents, urea, etc., and are highly soluble [Safarnejad, 2011]. Thus, nanobodies are particularly cytosol-tolerant and promising for use in antibody detection and attenuation of viral proteins.

In particular, begomoviruses are known to be widespread damaging pathogens to crops, particularly in the tropics and subtropics. Particularly damaging begomoviruses in tomato crops include Tomato Leaf Curl Sudan Virus (ToLCSDV) and Tomato Yellow Leaf Curl Virus (TYLCV) [Al-Saleh, 2014].

Thus, a nanobody against ToLCSDV and other begomoviruses and applications thereof solving the aforementioned problems are desired.

SUMMARY

A nanobody directed against begomoviruses is capable of selectively binding to ToLCSDV viral particles, TYLCV particles, and/or other begomoviruses. The nanobody includes an amino acid sequence of SEQ ID NO: 2.

These and other features of the present disclosure will become readily apparent upon further review of the following specification and drawings.

BRIEF DESCRIPTION OF THE DRAWINGS

FIG. 3 is a graph depicting experimental results confirming exemplary nanobody binding to ToLCSDV by solution competition.

Similar reference characters denote corresponding features consistently throughout the attached drawings.

DETAILED DESCRIPTION OF THE PREFERRED EMBODIMENTS

Figure 1:
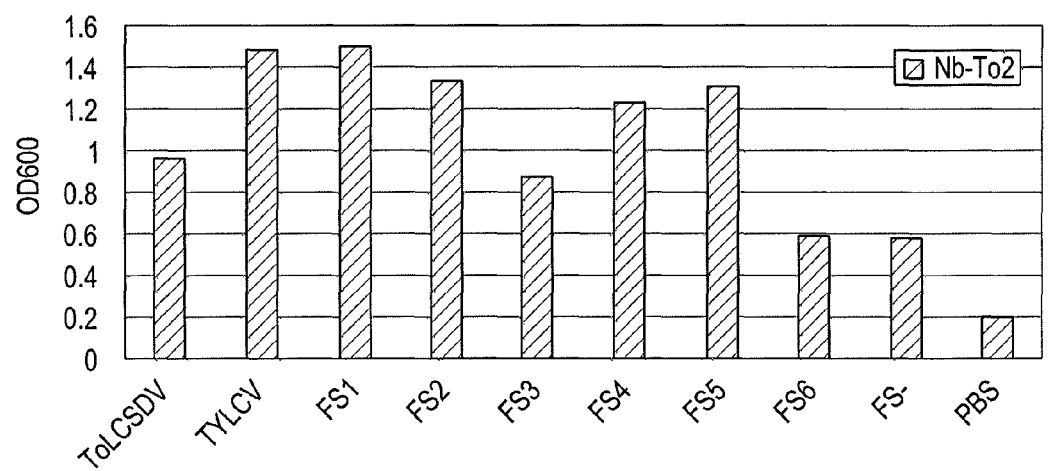
FIG. 1 is a graph depicting results of ELISA tests of an exemplary nanobody of the present application against field samples and control to demonstrate specificity of binding.

A nanobody against begomoviruses (herein, "Nb-To2") in an exemplary embodiment of the present subject matter is capable of specifically binding to Tomato Leaf Curl Sudan Virus (herein, "ToLCSDV") and Tomato Yellow Leaf Curl Virus (herein, "TYLCV"). The nanobody can be used to detect a begomovirus in a plant or plant part. The nanobody may be cloned into transgenic plants to provide resistance to ToLCSDV, TYLCV, and other begomoviruses' infections.

As used herein, the terms "nanobody", "VHH", "VHH antibody fragment" and "single domain antibody" are used indifferently and designate the variable domain of the single heavy chain of antibodies of the type of those found in Camelidae, which are naturally without any light chains. The nanobodies may in particular be nanobodies of camels, dromedaries, llamas or alpacas.

The nanobody directed against begomoviruses has a very strong affinity for ToLCSDV, and also binds very strongly to TYLCV as well as other begomoviruses. A "nanobody directed against begomoviruses", as used herein, refers to a nanobody capable of selectively binding to ToLCSDV viral particles, TYLCV particles, and/or other begomoviruses.

The nanobody can include the following amino acid sequence (SEQ ID NO: 2)
QVQLQESGGGSVQAGGSLRLSCVASGDTLRLCRMGWYRQAPGKGRELVSS

MEIDGTTNYADSVKGRFTISQGDNRNTMYLQMNSLKPEDTAMYYCKMEGG

YGGNCRLAIYNYWGQGTQVTVSS;

or a functional fragment thereof.

According to an embodiment, the nanobody is a nanobody comprising or consisting of the amino acid sequence of SEQ ID NO: 2.

The nanobody is encoded by a polynucleotide comprising a sequence of:

(SEQ ID NO.: 1)
TACCTATTGCCTACGGCAGCCGCTGGATTGTTATTACTCGCGGCCCAGCC

GGCCATGGCCCAGGTGCAGCTGCAGGAGTCTGGAGGAGGCTCGGTGCAGG

CTGGAGGGTCTCTGAGACTCTCCTGTGTAGCCTCTGGAGACACCTTGCGT

CTATGTCGCATGGGCTGGTACCGCCAGGCTCCAGGGAAGGGGCGYGAGTT

GGTCTCAAGTATGGAGATTGATGGTACTACAAACTATGCGGACTCCGTGA

AGGGCCGATTCACCATCTCCCAAGGCGACAATAGGAACACGATGTATCTG

CAAATGAACAGCCTGAAACCTGAGGACACGGCCATGTATTACTGCAAGAT

GGAAGGGGGATACGGTGGTAATTGTCGGCTTGCTATTT ATAACTATTGG

GGCCAGGGGACCCAGGTCACCGTCTCCTCA;

or a functional fragment thereof.

An embodiment of the present subject matter relates to a composition comprising at least one polypeptide encoding a variable domain of a heavy-chain antibody (VHH) or a functional fragment thereof capable of specifically binding to a begomovirus.

The begomovirus can include at least one of Tomato Leave Curl Sudan Virus (ToLCSDV) and Tomato Yellow Leaf Curl Virus (TYLCV). Specifically, the at least one polypeptide of the composition may include a sequence of:

(SEQ ID NO: 2)
QVQLQESGGGSVQAGGSLRLSCVASGDTLRLCRMGWYRQAPGKGRELVSS

MEIDGTTNYADSVKGRFTISQGDNRNTMYLQMNSLKPEDTAMYYCKMEGG

YGGNCRLAIYNYWGQGTQVTVSS.

The composition may include an agrochemically or pharmaceutically suitable carrier. For example, the composition can include about 0.0001% to about 50% by weight of the at least one polypeptide and an agrochemically or pharmaceutically suitable carrier. The composition may include a detectable marker. The composition may be applied to a plant or part to protect or treat the plant or plant part from a biological interaction with the begomovirus. The composition may be administered under conditions effective to protect or treat the plant or plant part against the biological interaction with the begomovirus. The plant can include harvested and unharvested plants. The plant can include a tomato plant.

The at least one polypeptide of the composition may be encoded by a polynucleotide comprising a sequence of:

(SEQ ID NO: 1)
TACCTATTGCCTACGGCAGCCGCTGGATTGTTATTACTCGCGGCCCAGCC

GGCCATGGCCCAGGTGCAGCTGCAGGAGTCTGGAGGAGGCTCGGTGCAGG

CTGGAGGGTCTCTGAGACTCTCCTGTGTAGCCTCTGGAGACACCTTGCGT

CTATGTCGCATGGGCTGGTACCGCCAGGCTCCAGGGAAGGGGCGYGAGTT

GGTCTCAAGTATGGAGATTGATGGTACTACAAACTATGCGGACTCCGTGA

AGGGCCGATTCACCATCTCCCAAGGCGACAATAGGAACACGATGTATCTG

CAAATGAACAGCCTGAAACCTGAGGACACGGCCATGTATTACTGCAAGAT

GGAAGGGGGATACGGTGGTAATTGTCGGCTTGCTATTT ATAACTATTGG

GGCCAGGGGACCCAGGTCACCGTCTCCTCA;

or a functional fragment thereof.

In another embodiment of the present subject matter, a transgenic plant, plant tissue or plant cell comprises at least one polynucleotide a sequence of:

(SEQ ID NO: 1)
TACCTATTGCCTACGGCAGCCGCTGGATTGTTATTACTCGCGGCCCAGCC

GGCCATGGCCCAGGTGCAGCTGCAGGAGTCTGGAGGAGGCTCGGTGCAGG

CTGGAGGGTCTCTGAGACTCTCCTGTGTAGCCTCTGGAGACACCTTGCGT

CTATGTCGCATGGGCTGGTACCGCCAGGCTCCAGGGAAGGGGCGYGAGTT

GGTCTCAAGTATGGAGATTGATGGTACTACAAACTATGCGGACTCCGTGA

AGGGCCGATTCACCATCTCCCAAGGCGACAATAGGAACACGATGTATCTG

CAAATGAACAGCCTGAAACCTGAGGACACGGCCATGTATTACTGCAAGAT

GGAAGGGGGATACGGTGGTAATTGTCGGCTTGCTATTT ATAACTATTGG

GGCCAGGGGACCCAGGTCACCGTCTCCTCA;

or a functional fragment thereof.

The transgenic plant may be a tomato plant. The transgenic plant may be a harvested or unharvested plant. The plant tissue or plant cell may be that of a tomato plant or other plant.

Another embodiment of the present subject matter includes a method of inhibiting or attenuating the begomovirus in a plant. The plant may be a harvested or unharvested plant. The plant may be a tomato plant. The method includes at least applying to a plant or to a plant part a composition including the amino acid of SEQ ID NO.:2 in an amount sufficient to attenuate an infection of the begomovirus in the plant or plant part.

Another embodiment of the present subject matter includes a method of detecting a plant virus in a plant. The plant may be a harvested or unharvested plant. The plant may be a tomato plant. The method includes applying to a plant or plant part a composition including the amino acid of SEQ ID NO.:2 and a detectable marker.

The following examples illustrate the present teachings.

Example 1

Exemplary Nanobody Isolation and Evaluation

Tomato plants exhibiting yellowing, leaf curl and stunting from Usfan, Saudi Arabia were collected and characterized using biological, serological and molecular methods. Agroinfectious clone of ToLCSDV was cloned from the collected plants. Following the inoculation of tobacco plants, the ToLCSDV viral particles were purified from symptomatic plants using sucrose density gradient. The purified antigen (ToLCSDV particles) was injected into Arabian camel (*Camelus dromedaries*) to generate immune response. The blood lymphocytes of the immunized Arabian camel were used to build VHH phage display library from the heavy chain antibodies (HCAbs). A library of around 2×10$^7$ independent transformants was obtained. The purified viral particles were used to isolate specific nanobodies from the VHH library using phage display technology. Here, we summarize the results of the isolated Nb-To2.

The DNA sequence of the isolated Nb-To2 gene is as follows:

(SEQ ID NO: 1)
TACCTATTGCCTACGGCAGCCGCTGGATTGTTATTACTCGCGGCCCAGCC

GGCCATGGCCCAGGTGCAGCTGCAGGAGTCTGGAGGAGGCTCGGTGCAGG

CTGGAGGGTCTCTGAGACTCTCCTGTGTAGCCTCTGGAGACACCTTGCGT

CTATGTCGCATGGGCTGGTACCGCCAGGCTCCAGGGAAGGGGCGYGAGTT

GGTCTCAAGTATGGAGATTGATGGTACTACAAACTATGCGGACTCCGTGA

AGGGCCGATTCACCATCTCCCAAGGCGACAATAGGAACACGATGTATCTG

CAAATGAACAGCCTGAAACCTGAGGACACGGCCATGTATTACTGCAAGAT

GGAAGGGGGATACGGTGGTAATTGTCGGCTTGCTATTTAT AACTATTGG

GGCCAGGGGACCCAGGTCACCGTCTCCTCA.

The resulting amino acid sequence encoded by the above Nb-To2 gene is:

(SEQ ID NO: 2)
QVQLQESGGGSVQAGGSLRLSCVASGDTLRLCRMGWYRQAPGKGRELVSS

MEIDGTTNYADSVKGRFTISQGDNRNTMYLQMNSLKPEDTAMYYCKMEGG

YGGNCRLAIYNYWGQGTQVTVSS.

Nb-To2 was purified by IMAC affinity using the 6×His tag. Successful purification was confirmed by SDS-PAGE analyses with commasie staining and western blotting using alkaline phosphatase conjugated monoclonal anti-polyHistidine antibody (Sigma) for detection.

Example 2

Nanobody Reactivity

Purified Nb-To2 was able to recognize not only purified Tomato Leave Curl Sudan Virus (ToLCSDV) but also purified Tomato Yellow Leave Curl Virus (TYLCV) begomovirus in both ELISA analysis (FIG. 1) and dot blot analysis (not shown). Additionally, Nb-To2 showed reactivity with extracts from tomato leaves showing the typical symptoms of begomovirus-infected plants collected from different locations in Riyadh, Saudi Arabia.

FIG. 1 depicts results of ELISA tests of Nb-To2 against field samples. FS1-6 are separate samples taken from tomato leaves showing the typical symptoms of Geminiviruses from different locations. FS— is a control sample of healthy tomato leave. Purified particles of ToLCSDV and TYLCV were also tested as controls.

Using Surface Plasmon Resonance (SPR) Analysis, the affinity and kinetic rate constants of Nb-To2 were determined (Table 1). The results of the single-cycle-kinetics of Nb-To2 to captured ToLCSDV shows high affinity of $K_D=290$ pM with fast association rate of $k_{ass}=4.7\ 10^6 \cdot M^{-1}s^{-1}$ and medium dissociation rate of $k_{diss}=1.4\ 10^{-3} \cdot s^{-1}$.

TABLE 1

Affinity and kinetic rate constants of Nb-To2 binding to captured ToLCSDV.

| $R_{Capture}$ | $k_{ass}$ | $k_{diss}$ | $K_D$ | $R_{max}$ | C hi$^2$ |
|---|---|---|---|---|---|
| 185 RU | $4.65\ 10^6 \cdot M^-1_S -1$ | $1.35\ 10^- 3._S -1$ | 292 pM | 6.82 RU | 0.022 |
| 310 RU | $4.05\ 10^6 \cdot M^-1_S -1$ | $1.51\ 10^- 3._S -1$ | 374 pM | 11.8 4 RU | 0.053 |
| 405 RU | $3.72\ 10^6 \cdot M^-1_S -1$ | $1.61\ 10^- 3._S -1$ | 432 pM | 17.1 2 RU | 0.118 |

Figure 2:
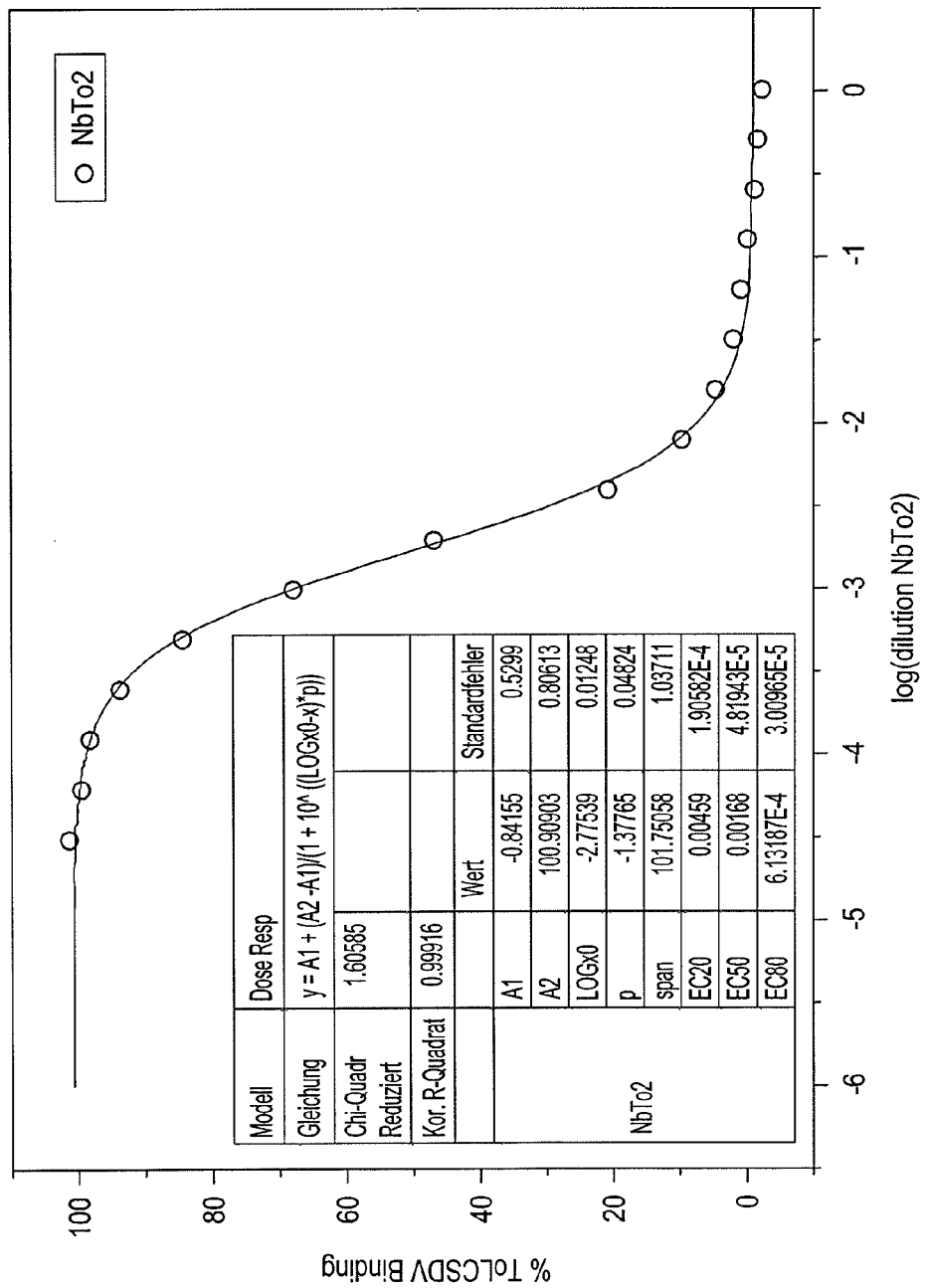
FIG. 2 is a graph depicting experimental results confirming exemplary nanobody binding to ToLCSDV by solution competition.
Figure 3:
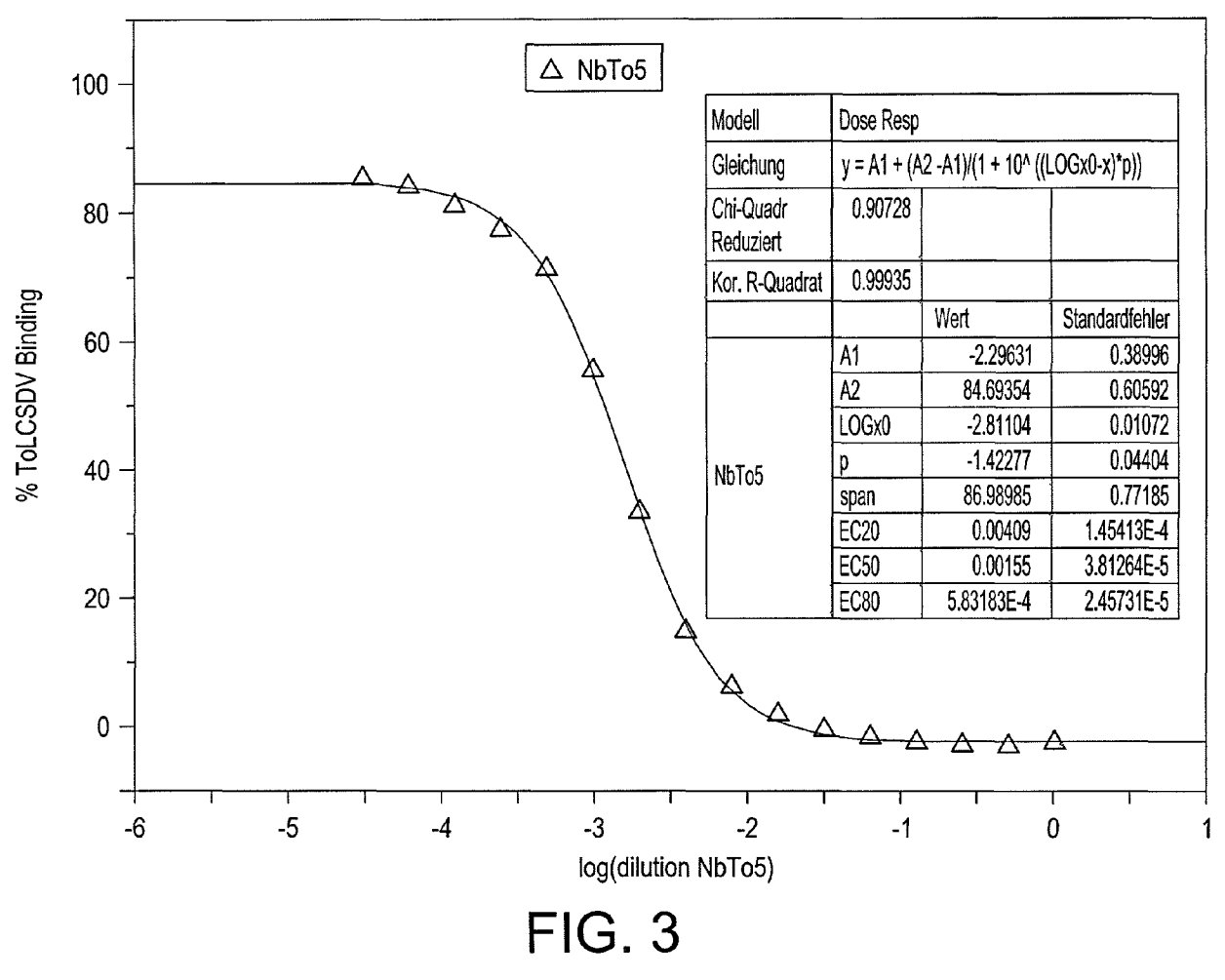

FIGS. 2-3 depict results from a competition experiment performed using soluble Nb-To2 and soluble Nb-To5 (another ToLCSDV-specific nanobody) to inhibit the binding of ToLCSDV to immobilized Nb-To5. Nb-To2 and Nb-To5 showed similar $IC_{50}$, or to be more precise $ID_{50}$ of −3.775 and −3.811 and p values of 1.377 and 1.423 respectively, meaning that 50% inhibition was observed using a 1:5956 and 1:6471 dilutions of the nanobody sample. Assuming a concentration of the nanobodies of 0.2 mg/mL this translate to an $IC_{50}$ concentration value of 30-35 ng/mL. These results further confirm binding of the Nb-To2 to ToLCSDV.

Specifically, FIGS. 2-3 show results of a 1:25 dilution of ToLCSDV incubated with a two-fold serial dilution of the nanobodies and the subsequent inhibition of binding to immobilized Nb-To5. The binding data was evaluated using a dose-response model with the equation $Y=A1+(A2-A1)/(1+10^{((\log x_0-x)^p)})$, where p represents a measure for positive or negative cooperativity and $\log x_0$ denotes the concentration/dilution at which 50% of the binding signal is inhibited.

The results demonstrate that the two nanobodies, Nb-To2 and Nb-To5, specifically bind to ToLCSDV with high affinity. Note that one can reasonably expect that nanobodies accumulate to 10 µg/mL or higher when expressed in the secretory pathway in plants, which, given the high affinity of the nanobody, would be high enough to efficiently neutralize ToLCSDV.

It is to be understood that the nanobody against begomoviruses is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A nanobody directed against a begomovirus, comprising the amino acid sequence of SEQ ID NO.: 2.

2. The nanobody according to claim 1, wherein the begomovirus includes at least one of Tomato Leaf Curl Sudan Virus (ToLCSDV) and Tomato Yellow Leaf Curl Virus (TYLCV).

3. A composition comprising at least one polypeptide having the amino acid sequence of SEQ ID NO: 2.

4. The composition according to claim 3, further comprising a detectable marker.

5. The composition according to claim 3, further comprising an agrochemical or pharmaceutically acceptable carrier.

6. The composition according to claim 3, comprising:
   about 0.0001% to about 50% by weight of the at least one polypeptide; and
   an agrochemically or pharmaceutically suitable carrier.

7. A method of inhibiting or attenuating a plant virus, the method comprising applying to a plant or to a part of said plant, the composition of claim 3.

8. A method of detecting infection by a plant virus, the method comprising:
   applying to a plant or to a part of said plant the composition according to claim 3.

9. A method for protecting or treating a plant or plant part from a biological interaction with a plant pest, the method comprising:
   applying to the plant or plant part, the composition according to claim 3 under conditions effective to protect or treat the plant or plant part against the biological interaction with the plant pathogenic virus.

10. A method for protecting a harvested plant or a harvested plant part from a biological interaction with a plant virus, the method comprising:
    applying to the harvested plant or harvested plant part, the composition of claim 3, under conditions effective to protect the harvested plant or harvested plant part against the biological interaction with the plant virus.

11. A transgenic plant comprising at least one polynucleotide having the sequence of SEQ ID NO: 1.

12. The transgenic plant according to claim 11, wherein the transgenic plant is a tomato plant.

* * * * *

SEQUENCE LISTING

<160> NUMBER OF SEQ ID NOS: 2

<210> SEQ ID NO 1
<211> LENGTH: 429
<212> TYPE: DNA
<213> ORGANISM: Camelus dromedarius

<400> SEQUENCE: 1
tacctattgc ctacggcagc cgctggattg ttattactcg cggcccagcc ggccatggcc        60

```
caggtgcagc tgcaggagtc tggaggaggc tcggtgcagg ctggagggtc tctgagactc    120
tcctgtgtag cctctggaga caccttgcgt ctatgtcgca tgggctggta ccgccaggct    180
ccagggaagg ggcgygagtt ggtctcaagt atggagattg atggtactac aaactatgcg    240
gactccgtga agggccgatt caccatctcc caaggcgaca ataggaacac gatgtatctg    300
caaatgaaca gcctgaaacc tgaggacacg gccatgtatt actgcaagat ggaaggggga    360
tacggtggta attgtcggct tgctatttat aactattggg gccagggggac ccaggtcacc    420 gtctcctca                                                           429

<210> SEQ ID NO 2
<211> LENGTH: 123
<212> TYPE: PRT
<213> ORGANISM: Camelus dromedarius

<400> SEQUENCE: 2

Gln Val Gln Leu Gln Glu Ser Gly Gly Gly Ser Val Gln Ala Gly Gly
1               5                   10                  15

Ser Leu Arg Leu Ser Cys Val Ala Ser Gly Asp Thr Leu Arg Leu Cys
            20                  25                  30

Arg Met Gly Trp Tyr Arg Gln Ala Pro Gly Lys Gly Arg Glu Leu Val
        35                  40                  45

Ser Ser Met Glu Ile Asp Gly Thr Thr Asn Tyr Ala Asp Ser Val Lys
    50                  55                  60

Gly Arg Phe Thr Ile Ser Gln Gly Asp Asn Arg Asn Thr Met Tyr Leu
65                  70                  75                  80

Gln Met Asn Ser Leu Lys Pro Glu Asp Thr Ala Met Tyr Tyr Cys Lys
            85                  90                  95

Met Glu Gly Gly Tyr Gly Gly Asn Cys Arg Leu Ala Ile Tyr Asn Tyr
            100                 105                 110

Trp Gly Gln Gly Thr Gln Val Thr Val Ser Ser
            115                 120
```